US011918336B2

(12) United States Patent
Laleg et al.

(10) Patent No.: US 11,918,336 B2
(45) Date of Patent: Mar. 5, 2024

(54) REDUCED FEATURE GENERATION FOR SIGNAL CLASSIFICATION BASED ON POSITION WEIGHT MATRIX

(71) Applicant: KING ABDULLAH UNIVERSITY OF SCIENCE AND TECHNOLOGY, Thuwal (SA)

(72) Inventors: Taous Meriem Laleg, Thuwal (SA); Fahad Ali Albalawi, Thuwal (SA); Abderrazak Chahid, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 392 days.

(21) Appl. No.: 17/430,109

(22) PCT Filed: Feb. 14, 2020

(86) PCT No.: PCT/IB2020/051272
§ 371 (c)(1),
(2) Date: Aug. 11, 2021

(87) PCT Pub. No.: WO2020/170101
PCT Pub. Date: Aug. 27, 2020

(65) Prior Publication Data
US 2022/0147756 A1 May 12, 2022

Related U.S. Application Data

(60) Provisional application No. 62/893,452, filed on Aug. 29, 2019, provisional application No. 62/807,511, filed on Feb. 19, 2019.

(51) Int. Cl.
*A61B 5/055* (2006.01)
*A61B 5/00* (2006.01)
(Continued)

(52) U.S. Cl.
CPC ............ *A61B 5/055* (2013.01); *A61B 5/0042* (2013.01); *G06F 18/2431* (2023.01);
(Continued)

(58) Field of Classification Search
CPC ..... A61B 5/055; A61B 5/0042; A61B 5/7267; A61B 2576/026; A61B 5/4088;
(Continued)

(56) References Cited

U.S. PATENT DOCUMENTS 9,449,392 B2 * 9/2016 Han .................... G06V 10/7625
9,600,138 B2 * 3/2017 Thomas ................. G06T 19/20
(Continued)

FOREIGN PATENT DOCUMENTS

WO   WO-03066041 A1 *  8/2003  .......... A23L 33/175
WO   WO-2015161363 A1 * 10/2015  .......... A61B 5/0042
WO   WO-2017062382 A1 *  4/2017  .......... G06K 9/4628

OTHER PUBLICATIONS

Cabral, C., et al., "Decoding Visual Brain States from fMRI using an Ensemble of Classifiers," Pattern Recognition, May 7, 2012, vol. 45, pp. 2064-2074, Elsevier Ltd.
(Continued)

*Primary Examiner* — Mahendra R Patel
(74) *Attorney, Agent, or Firm* — PATENT PORTFOLIO BUILDERS PLLC

(57) ABSTRACT

A method for classifying input data includes receiving the input data that describe an object, wherein the input data corresponds to plural classes; associating the input data with voxels that describe the object; calculating a real-number sequence X(n), which is associated with a measured parameter P that describes the object; quantizing the real-number sequence X(n) to generate a finite set sequence Q(n), where n describes a number of levels; generating a voxel-based weight matrix for each class of the input data; and calcu-
(Continued)

lating a score S for each class of the plural classes, based on a corresponding voxel-based weight matrix. The score S is a number that indicates a likelihood that the input data associated with a given sample belongs to a class of the plural classes.

20 Claims, 9 Drawing Sheets

(51) Int. Cl.
 *G06F 18/2431* (2023.01)
 *G06T 7/00* (2017.01)
 *G06T 11/00* (2006.01)
(52) U.S. Cl.
 CPC .......... *G06T 7/0012* (2013.01); *G06T 11/008* (2013.01); *A61B 5/7267* (2013.01); *A61B 2576/026* (2013.01); *G06F 2218/12* (2023.01); *G06T 2207/10088* (2013.01); *G06T 2207/30016* (2013.01)
(58) Field of Classification Search
 CPC ... A61B 5/7225; A61B 5/7275; A61B 5/4064; G06F 18/2431; G06F 2218/12; G06F 18/2134; G06T 7/0012; G06T 11/008; G06T 2207/10088; G06T 2207/30016
 USPC ......................................................... 382/131
 See application file for complete search history.

(56) References Cited

U.S. PATENT DOCUMENTS

| | | | | |
|---|---|---|---|---|
| 9,760,807 | B2* | 9/2017 | Zhou | G06V 30/194 |
| 10,452,989 | B2* | 10/2019 | Majumdar | G06N 10/00 |
| 2004/0013292 | A1* | 1/2004 | Raunig | G06T 7/45 |
| | | | | 382/128 |
| 2009/0143669 | A1* | 6/2009 | Harms | G16H 50/20 |
| | | | | 600/410 |
| 2013/0211227 | A1* | 8/2013 | Pettegrew | A61K 31/22 |
| | | | | 600/407 |
| 2013/0211229 | A1* | 8/2013 | Rao | A61B 5/055 |
| | | | | 600/410 |
| 2013/0304710 | A1* | 11/2013 | Nachev | G06F 16/30 |
| | | | | 707/690 |
| 2015/0272467 | A1* | 10/2015 | Warfield | G01R 33/54 |
| | | | | 382/131 |
| 2016/0343127 | A1* | 11/2016 | Miller | G06T 7/11 |
| 2018/0285731 | A1* | 10/2018 | Heifets | G06N 3/04 |
| 2018/0333068 | A1* | 11/2018 | Beck | A61B 5/055 |

OTHER PUBLICATIONS

Ramakrishna, J.S., et al., , "Classification of Cognitive State using Statistics of Split Time Series," in India Conference (INDICON), 2016 IEEE Annual, Dec. 16-18, 2016, pp. 1-5, IEEE.

Albalawi, F., et al., Hybrid Model for Efficient Prediction of Poly(A) Signals in Human Genomic DNA,) Methods, Apr. 13, 2019, vol. 166, pp. 31-39, Elsevier Inc.

Gray, R.M., et al., "Quantization," IEEE Transactions on Information Theory, Oct. 1998, vol. 44, No. 6, pp. 2325-2383, IEEE.

International Search Report in corresponding/related International Application No. PCT/IB2020/051272, dated Jun. 29, 2020.

Mitchell, T.M., et al., "Learning to Decode Cognitive States from Brain Images," Machine Learning, Oct. 2004, vol. 57, pp. 145, 175, Kluwer Academic Publishers.

Ramasangu, H., et al., "Cognitive State Classification Using Transformed fMRI Data," 2014 International Conference on Signal Processing and Communications (SPCOM), IEEE, Jul. 22, 2014, pp. 1-5, IEEE.

Sinha, S., "On Counting Position Weight Matrix Matches in a Sequence, Application to Discriminative Motif Finding," Bioformatics, Aug. 2006, vol. 22, No. 14, pp. e454-e463, Oxford University Press.

Wang, X., et al., "Using Machine Learning to Detect Cognitive States cross Multiple Subjects," Center for Automated Learning and Discovery, School of Computer Science, Carnegie Mellon University, 2002, pp. 1-13.

Written Opinion of the International Searching Authority in corresponding/related International Application No. PCT/IB2020/051272, dated Jun. 29, 2020.

* cited by examiner

Algorithm 1 Uniform Quantizer Algorithm

Input : $X$: Real-valued voxel sequence $M$: Number of Quantization levels $\mu$: Quantization centroide $r$: Quantization resolution

Output : $Q$: Integer valued voxel sequence $N_X \leftarrow$ length of $X$ for $n \leftarrow 1$ to $N_X$ do for $k \leftarrow \dfrac{2-M}{2}$ to $\dfrac{M}{2}$ do if $X(n) < \mu + \dfrac{(2-M)\,r}{2}$ then

$Q(n) = q_1$;

else if $\mu + (k-1)\,r \leq X(n) < \mu + k\,r$ then

$Q(n) = q(k + M/2)$;

else

$Q(n) = q_M$;

end end

FIG. 4

| Star/plus Subject | Method1 ([14]) | | | Method2 ([26]) | | | VW method [M = 6, r = σ] | | |
|---|---|---|---|---|---|---|---|---|---|
| | classifier | feature size | Accuracy | classifier | feature size | Accuracy | classifier | feature size | Accuracy |
| 4799 | NB | 4080 | 45 | SVM | 255 | 99 | LR | 2 | 100 |
| 4820 | NB | 6528 | 90 | SVM | 408 | 89 | LR | 2 | 100 |
| 4847 | NB | 5088 | 100 | SVM | 318 | 100 | LR | 2 | 100 |
| 5675 | NB | 6384 | 95 | SVM | 399 | 98 | LR | 2 | 100 |
| 5680 | NB | 5344 | 95 | SVM | 334 | 100 | LR | 2 | 98.7 |
| 5710 | NB | 3504 | 100 | SVM | 219 | 99 | LR | 2 | 100 |
| Average | - | 5155 | 87.50 | - | 322 | 97.50 | - | 2 | 99.8 |

FIG. 6

| Star/plus Subject | Method1 ([14]) | | | Method2 ([26]) | | | VW method [M = 6, r = σ] | | |
|---|---|---|---|---|---|---|---|---|---|
| | classifier | feature size | Accuracy | classifier | feature size | Accuracy | classifier | feature size | Accuracy |
| 4820 | NB | 12240 | 82.5 | SVM | 755 | 100 | LR | 2 | 100 |
| 4847 | NB | 26100 | 98.75 | SVM | 1600 | 100 | LR | 2 | 99.3 |
| 4799 | NB | 19400 | 98.75 | SVM | 1150 | 93 | LR | 2 | 98.11 |
| 5675 | NB | 24000 | 97.5 | SVM | 1350 | 95 | LR | 2 | 100 |
| 5680 | NB | 18222 | 96.25 | SVM | 1250 | 97 | LR | 2 | 96.1 |
| 5710 | NB | 12231 | 95 | SVM | 733 | 100 | LR | 2 | 100 |
| Average | - | 18699 | 94.79 | - | 1140 | 97.5 | - | 2 | 98.92 |

FIG. 7

| Star/plus | Method1 ([14]) | | | Method2 ([26]) | | | VW method [$M = 6, r = \sigma$] | | |
|---|---|---|---|---|---|---|---|---|---|
| Subject | classifier | feature size | Accuracy | classifier | feature size | Accuracy | classifier | feature size | Accuracy |
| 4820 | NB | 15630 | 88.75 | SVM | 987 | 100 | LR | 2 | 97.1 |
| 4847 | NB | 30878 | 100 | SVM | 1989 | 97 | LR | 2 | 98.2 |
| 4799 | NB | 25321 | 93.75 | SVM | 1656 | 90 | LR | 2 | 100 |
| 5675 | NB | 32121 | 93.75 | SVM | 1545 | 95 | LR | 2 | 100 |
| 5680 | NB | 23456 | 91.25 | SVM | 1456 | 95 | LR | 2 | 99.22 |
| 5710 | NB | 16544 | 93.75 | SVM | 1090 | 100 | LR | 2 | 94.23 |
| Average | - | 23992 | 93.54 | - | 1454 | 96.17 | - | 2 | 98.13 |

FIG. 8

| M \ ασ | 0.2σ | 0.4σ | 0.6σ | 0.8σ | σ | 1.2σ | 1.4σ | 1.6σ | 1.8σ | 2σ |
|---|---|---|---|---|---|---|---|---|---|---|
| 4 | 0.91 | 0.92 | 0.84 | 0.84 | 1 | 0.98 | 0.92 | 0.84 | 0.83 | 0.83 |
| 6 | 0.90 | 0.6625 | 0.67 | 1 | 0.99 | 1 | 0.92 | 0.84 | 0.83 | 0.83 |
| 8 | 0.75 | 0.59 | 0.69 | 0.99 | 1 | 1 | 0.92 | 0.84 | 0.83 | 0.83 |
| 10 | 0.78 | 0.42 | 0.70 | 1 | 1 | 1 | 0.92 | 0.84 | 0.83 | 0.83 |
| 12 | 0.56 | 0.29 | 0.76 | 1 | 1 | 1 | 0.92 | 0.84 | 0.83 | 0.83 |
| 14 | 0.66 | 0.35 | 0.75 | 1 | 1 | 1 | 0.92 | 0.84 | 0.83 | 0.83 |

FIG. 9

REDUCED FEATURE GENERATION FOR SIGNAL CLASSIFICATION BASED ON POSITION WEIGHT MATRIX

CROSS-REFERENCE TO RELATED APPLICATIONS

This application is a U.S. National Stage Application of International Application No. PCT/IB2020/051272, filed on Feb. 14, 2020, which claims priority to U.S. Provisional Patent Application No. 62/807,511, filed on Feb. 19, 2019, entitled "REDUCED FEATURE GENERATION FOR SIGNAL CLASSIFICATION BASED ON POSITION WEIGHT MATRIX," and U.S. Provisional Patent Application No. 62/893,452, filed on Aug. 29, 2019, entitled "REDUCED FEATURE GENERATION FOR SIGNAL CLASSIFICATION BASED ON POSITION WEIGHT MATRIX," the disclosures of which are incorporated herein by reference in their entirety.

BACKGROUND

Technical Field

Embodiments of the subject matter disclosed herein generally relate to using artificial intelligence for classifying signals, and more specifically, to a feature generation method and device that extract a reduced number of pertinent and discriminative characteristics of a signal.

Discussion of the Background

With the advance of electronics, a large amount of data is generated today. This data, regardless of its type, i.e., health care, or photography, or social media, or agriculture, needs to be classified in order to be useful to humans. However, the task of classifying this data by a group of data analysts is today becoming overwhelming because not only the amount of data is large, but it is also complex and growing. Thus, there is a strong push in the Artificial Intelligence (AI) community to come with an automated system/method that is capable to process this large amount of data and automatically generate pertinent and discriminative characteristics associated with the data, such that the data can be automatically classified based on these characteristics and then presented to the user.

A specific field in which AI algorithms have been applied for classifying the collected data is the functional Magnetic Resonance Imaging (fMRI). fMRI has emerged as a powerful brain imaging modality that indirectly measures the brain activity with good spatial and temporal resolution. It provides three-dimensional scans of the brain per unit of time, which allows the detection of the activated regions as a response to a neural activity. Since its discovery, fMRI has been used for the detection and monitoring of neurological diseases and disorders such as Schizophrenia and Alzheimer disease.

fMRI captures the changes in the blood oxygen levels that occur in the activated regions of the brain, which provides a signal called Blood Oxygen Level Dependent (BOLD) signal. The BOLD signal is triggered by changes in the cerebral blood flow and reflects the increase in the deoxyhemoglobin content. The fMRI approach has been used in many clinical and research conditions, resulting in the generation of a huge amount of data. As a result, several studies have been focused recently on the use of data-driven approaches to analyze, interpret and extract relevant information from fMRI data. In addition, fMRI data were used to estimate parameters that help efficiently model the relation between a neural stimulus and the observed BOLD signal.

A particular interest has been on the development of machine learning methods to classify the cognitive state of a human subject based on fMRI data. For example, in [1], the authors decoded cognitive states that correspond to distinct tasks such as viewing a sentence/picture and reading an ambiguous/non-ambiguous sentence. The main challenge that the authors have addressed when decoding human cognitive states is the big discrepancy between the number of available samples for a given cognitive state and the dimension of the feature vectors. Therefore, optimal search techniques can be developed to choose an optimal feature vector with a well-suited classifiers.

Motivated by this, in [2], a cascade of classifiers that can improve the cognitive state prediction performance has been proposed. However, the issue of over-fitting associated with the fMRI data has not been considered. Therefore, a group of predictors named Generalized Sparse Classifiers (GSC) have been developed to address the issue of over-fitting caused by the high dimensional feature vector. The derived group of classifiers were applied to a benchmark dataset called star/plus [3] and achieved an average accuracy of 93.7%. An algorithm called Support Vector Decomposition Machine (SVDM), which combines feature selection and classification learning into one single step was developed. Although the SVDM was able to project the data into 8 features, its prediction performance to the star/plus dataset was poor, having an average accuracy of 78%. In [4], the authors have proposed a procedure to enable classification between two chosen cognitive tasks, using their respective fMRI image sequences. Different classification methods with two signal processing-based features were applied to the star/plus dataset where an average accuracy of 99% was obtained using the support vector machine algorithm. Even though the proposed method was able to achieve high prediction accuracy, the dimension of the extracted feature vector was extremely high. For classification purposes, it is highly desirable to utilize a low-dimensional feature vector when the number of observations (i.e., samples) used to generate a prediction model is small.

However, these methods are still computer- and time-intensive. Thus, there is a need for a new feature generation method that has a well-suited classifier that can both reduce the high-dimensional feature vector and improve the overall prediction performance, to overcome the above noted deficiencies of the traditional methods.

SUMMARY

According to an embodiment, there is a method for classifying input data. The method includes receiving the input data that describe an object, wherein the input data corresponds to plural classes; associating the input data with voxels that describe the object; calculating a real-number sequence $X(n)$, which is associated with a measured parameter P that describes the object; quantizing the real-number sequence $X(n)$ to generate a finite set sequence $Q(n)$, where n describes a number of levels; generating a voxel-based weight matrix for each class of the input data; and calculating a score S for each class of the plural classes, based on a corresponding voxel-based weight matrix. The score S is a number that indicates a likelihood that the input data associated with a given sample belongs to a class of the plural classes.

According to another embodiment, there is a computing device for classifying input data. The computing device includes an interface for receiving the input data that describe an object, wherein the input data corresponds to plural classes; and a processor connected to the interface. The processor is configured to associate the input data with voxels that describe the object; calculate a real-number sequence X(n) that describes a parameter P associated with the object; quantize the real-number sequence X(n) to generate a finite set sequence Q(n), where n describes a number of levels; generate a voxel-based weight matrix for each class of data; and calculate a score S for each class of the plural classes, based on a corresponding voxel-based weight matrix. The score S is a number that indicates a likelihood that the input data associated with a given sample belongs to a class of the plural classes.

BRIEF DESCRIPTION OF THE DRAWINGS

The accompanying drawings, which are incorporated in and constitute a part of the specification, illustrate one or more embodiments and, together with the description, explain these embodiments. In the drawings:

FIG. 4 illustrates an algorithm that quantizes the data;

FIGS. 6 to 8 illustrate results obtained with the novel method of generating a feature of the input data in comparison with the results obtained by two traditional methods;

FIG. 9 illustrates, in a table format, the sensitivity of the accuracy of the current method for different levels M of quantization and resolution factor;

DETAILED DESCRIPTION

Figure 1:
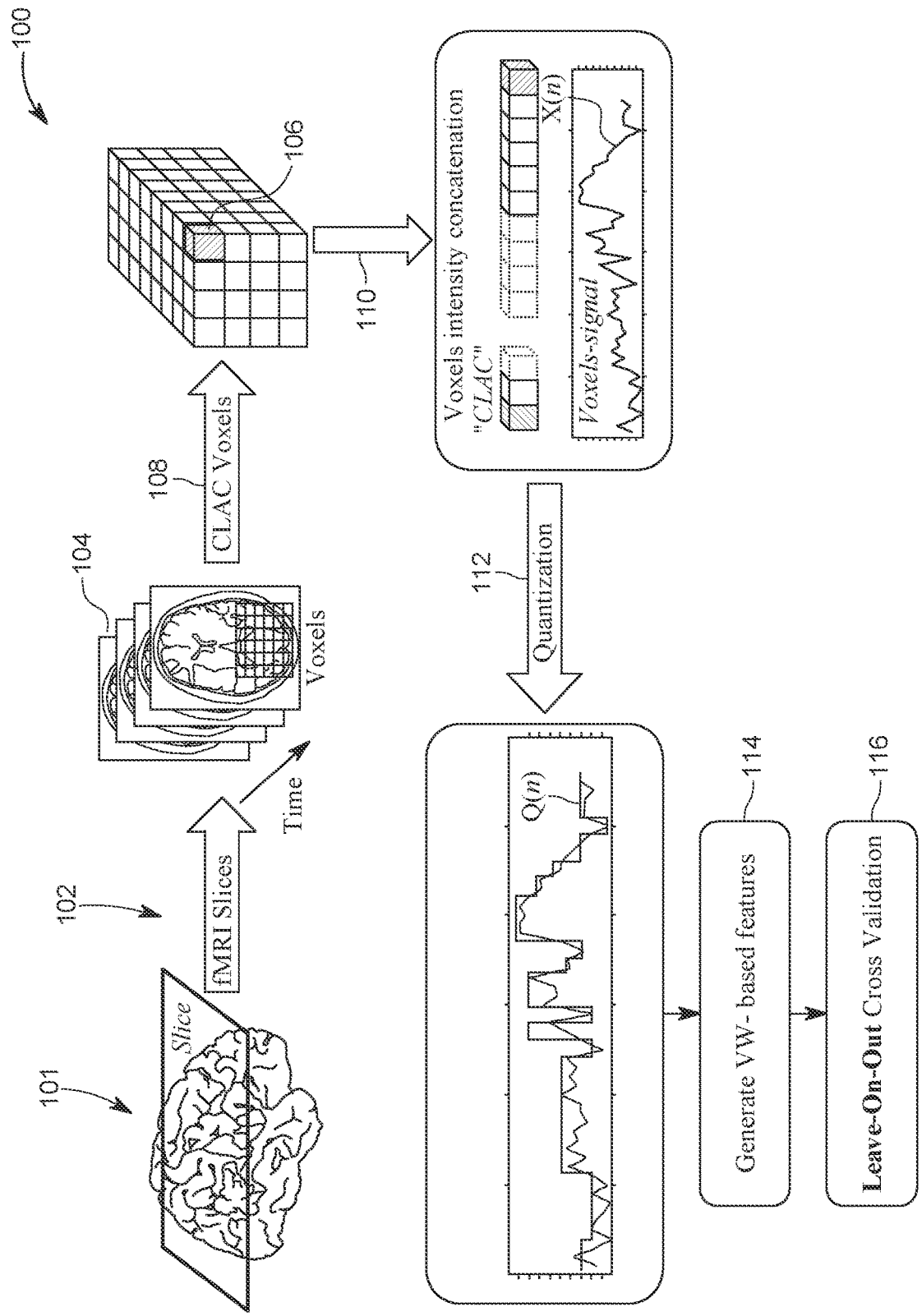
FIG. 1 schematically illustrates how information from brain is assembled and then quantized for generating a score.

The following description of the embodiments refers to the accompanying drawings. The same reference numbers in different drawings identify the same or similar elements. The following detailed description does not limit the invention. Instead, the scope of the invention is defined by the appended claims. The following embodiments are discussed, for simplicity, with regard to fMRI data. However, the methods discussed herein can also be applied to any type of data that need to be classified. For example, the methods discussed herein can be applied to water peak estimation, water suppression signal in magnetic resonance spectroscopy (MRS) signals, MRS signal denoising, pulse-shaped signal decomposition and denoising, etc. The novel methods can be integrated in any processing unit to process biomedical signals such as MRS signals, electroencephalogram (EEG) signals, or any other pulse-shaped signal.

Reference throughout the specification to "one embodiment" or "an embodiment" means that a particular feature, structure or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

According to an embodiment, a novel methodology that generates a set of features, termed voxel weight-based (VW-based) features, is introduced. This set of features can represent the voxel activity in the human brain when performing cognitive tasks. One advantage of this new feature set is its ability to project the high-dimensional voxels features vector into a two-dimensional feature domain. A star/plus dataset has been used to assess the performance of the proposed features when they are used to classify the two cognitive tasks. After generating the VW-based feature set, a logistic regression model (LRM) is utilized to distinguish between the two cognitive states that correspond to two distinct tasks (whether a subject is viewing a picture or a sentence). To demonstrate the efficacy of the proposed feature generation scheme, a benchmark fMRI dataset called start/plus dataset is utilized to assess the performance of the LRM under the proposed model. The LR model with the proposed two-dimensional feature vector outperformed the best two reported prediction models associated with the state/plus dataset with an average accuracy of 99.8%, as discussed later. While the embodiments discussed herein are referring to two brain activities, the methods discussed in these embodiments can be applied to other type of data, or to more than two activities. The two brain activities were selected for illustrating the novel method because there is available actual data associated with these activities, and also because other models have tried to extract the characteristics of these activities, and thus, the results of the novel method may be compared with the existing one for evaluating the accuracy of the novel method.

The star/plus dataset experiment proposed in [3] was used to demonstrate the proposed feature methodology. In such experiment, fMRI snapshots were obtained every half second (repetition time) when six subjects were performing two distinct cognitive tasks. Particularly, every subject first sees a sentence (semantic stimulus) or a picture (symbol stimulus) for 4 seconds, then a blank screen for 4 seconds is shown to the subject. Every sample is a collection of fMRI 8-seconds period: 4-seconds period of sentence or picture stimulus followed by 4-seconds period of blank screen. Following this strategy, a total of 80 samples are generated from each subject (40 samples for sentence class and 40 samples for picture class). Every sample includes 16 fMRI snapshots (8 snapshots corresponding to the sentence or picture stimulus and 8 snapshots corresponding to the blank screen), resulting in an input feature vector of size 16N, where N represents the number of active voxels in a particular Regions Of Interest (ROIs) when the subject sees either the picture or the sentence. Due to the variation of the brain morphology between subjects, the number of active voxels N within the ROIs is different for each subject. The dataset consists of 25 anatomically defined ROIs. As there are suggestions in the art that only 7 regions are important, fMRI datasets collected from those 7 ROIs and subsets of them where used to compare the performance of the proposed VW-based feature generation technique with respect to the best reported prediction models. Thus, the number of active voxels N can vary depending on the experiment and/or the subject.

The novel VW-based features generation method is schematically illustrated in FIG. 1 and includes a step 102 in which one or more slices of an object 101 (e.g., a brain in this implementation) are taken using MRI technology. Note that the method is not limited to MRI imagining, as other methods may be used to collect information about the object, for example, computer tomography, fluorescence, optical microscopy, etc. The collected slices 104 (i.e., the input data) are taken at various time intervals as discussed above, and they represent a 3D model of the sampled object 101. Then, plural voxels 106 for one ROI are selected in step 108. In step 110, a parameter P associated with the object 101 (for example, the voxel intensity in terms of the fMRI recorded signal, but other signals may also be used) is calculated to generate a real-number sequence $X(n)$. Note that the real-number sequence $X(n)$ corresponds to the values of the parameter P for the voxels in one or more ROIs, for a given sample. Then, in step 112, the real-number sequence $X(n)$ is quantized to generate a symbol sequence $Q(n)$. In step 114 the VW features are generated and in step 116 the generated features are used against an existing dataset to predict to which class the calculated parameter P belongs to. These steps are now discussed in more detail.

The novel VW-based features generation method illustrated in FIG. 1 uses a biological feature generation technique called Position Weight Matrix (PWM)-based features. Thus, a short overview of the PWM method is first provided and then this feature generation methodology is extended to generate the proposed VW-based features.

Position Weight Matrix (PWM)-based features extraction is used for motifs representation in DNA/RNA sequences. In this features extraction paradigm, two position weight matrices (PWMs) are often extracted from a set of aligned DNA/RNA sequences that are believed to be functionally related. This feature generation technique is used in many software tools for computational motif discovery. Traditionally, two PWMs are usually derived from two sets of aligned DNA sequences that are thought to be functionally related. Then, these two matrices are utilized to generate a number of features that may help improve the classification performance [5]. In order to construct the PWMs, the dataset or the samples have to belong to a finite set of integers or characters. Naturally, the DNA sequences are represented by a set of four characters, i.e., nucleotides A, C, G and T. To generate the two PWM matrices, two groups of DNA sequences that belong to two distinct classes are first aligned, then the probability of occurrence of each of the four DNA nucleotides (A, C, G, and T) is calculated at each position of the DNA sequence. The probability of occurrence of each DNA nucleotide in a certain position (A, C, G, or T) is equal to the number of occurrences of such nucleotide divided by the total number of sequences.

For example, assume that there are two sets of DNA sequences, where the length of each of the DNA sequence is 5. Then, the PWM for every class will be of size 4×5 and can have the following structure:

$$PWM = \begin{pmatrix} 0.4 & 0.2 & 0.6 & 0.25 & 0.4 \\ 0.3 & 0.2 & 0.1 & 0.25 & 0.1 \\ 0.1 & 0.2 & 0.1 & 0.25 & 0.4 \\ 0.2 & 0.4 & 0.2 & 0.25 & 0.1 \end{pmatrix} \quad (1)$$

In every column of the above PWM matrix, there are four probabilities that sum up to 1, where every element in that column indicates the probability of occurrence of one of the four DNA nucleotides.

The step of quantization 112 discussed with regard to FIG. 1 can be generally defined as a map q from an Euclidean space $R^d$ into a subset of symbols $\{a_1, a_2, \ldots, a_p\}$ of the same space. Thus, the map q can be used to convert a d-dimensional input signal $X(n)$ into an output sequence $Q(n)$ that can take on at most p different values [6], [7]. The quantization is utilized in this method to convert the parameter P, e.g., voxels intensity, described by the discrete sequence $X(n)$ to a symbol sequence $Q(n)$. In order to choose a suitable quantization scheme, the probability distribution of the real-valued discrete sequence Xn) is analyzed for both classes (i.e., picture and sentence).

Figure 2:
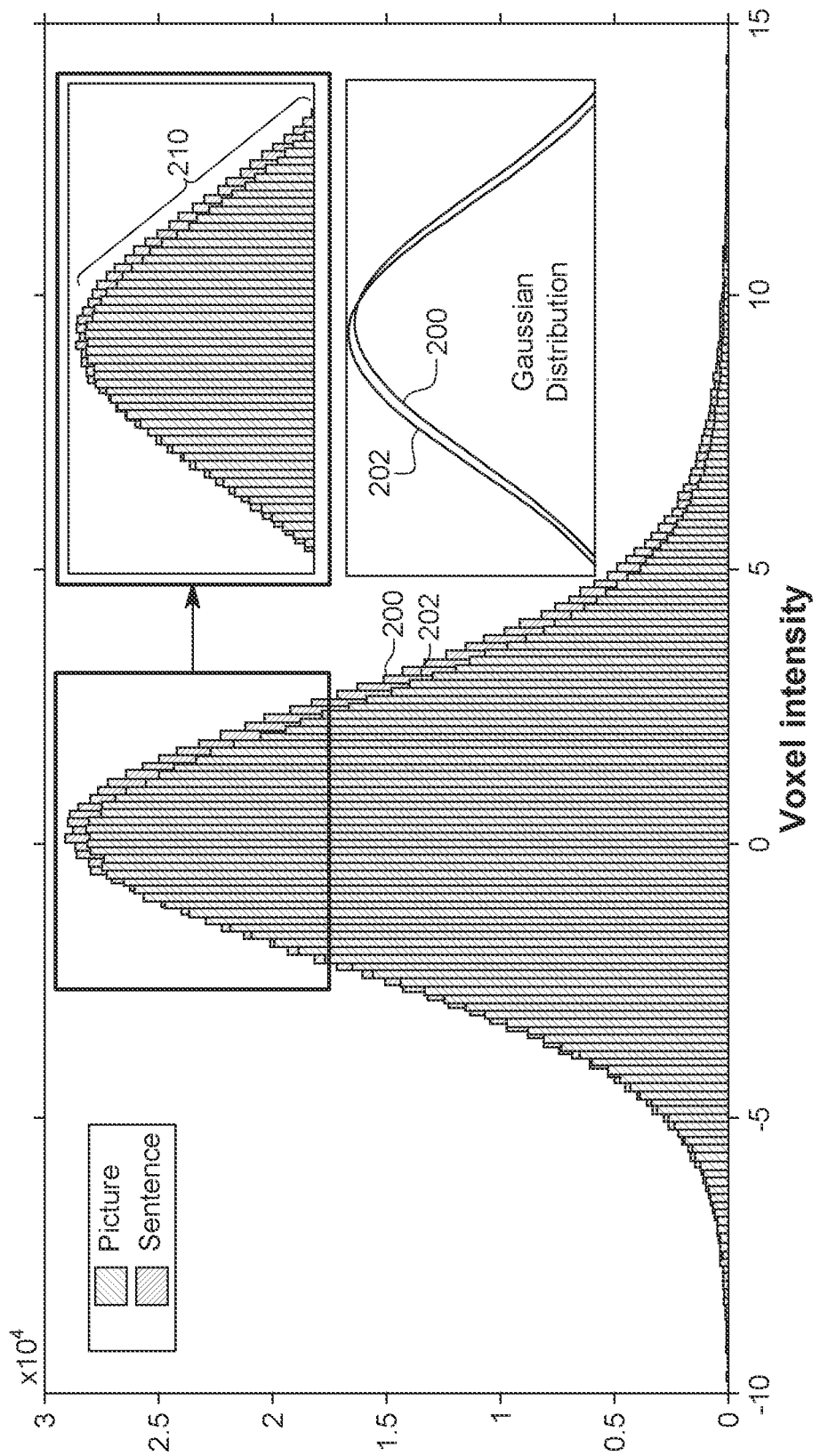
FIG. 2 illustrates the distribution of two classes of data collected for MRI imagining of the brain.

To do so, a histogram of the voxels intensity values of the six subjects is plotted for both classes (picture and sentence), as illustrated in FIG. 2. FIG. 2 shows the fitted Gaussian Probability Distribution Function (PDF) 200 and 202 (with 200 corresponding to the sentence voxel intensities and 202 to the picture voxel intensities) to the histogram plots for both classes, where the zoomed region shows where there is a discrepancy 210 between the two Gaussian distributions.

To quantify the voxels intensity values shown in FIG. 2 for both classes, a quantization scheme that can transform measured signal intensities forming the sequence $X(n)$, into a discrete symbol sequence $Q(n)$, is implemented.

Quantization is the process of mapping signals from a continuous set to output values in a (countable) smaller set. In one embodiment, the quantization mapping $F: R \rightarrow \Omega$ is defined as follows:

$$F(X) = \begin{cases} q_1 & \text{if } X < \mu + \frac{(2-M)r}{2} \\ q_{(k+M/2)} & \text{if } \mu + (k-1)r \leq X < \mu + kr \\ q_M & \text{elsewhere} \end{cases}$$

such that $$\Omega = \{q_1, q_2, \ldots q_M\}; k = \frac{-M}{2}+, \frac{-M}{2}+3, \ldots, \frac{M}{2}-1,$$

where $\mu$ and r are the centroid and the resolution of the quantization which will be defined later.

The mapping F is utilized to convert the voxels intensity discrete sequence $X(n)$ to a symbol sequence $Q(n)=F(X(n))$. In order to choose a suitable quantization scheme, first the probability distribution of the real-valued voxels intensity sequence are analyzed for both classes (i.e., picture and sentence). To do so, the histogram of the voxels intensity values of the six subjects for both classes is analyzed, i.e., a fitted Gaussian Probability Distribution Function (PDF) to the histogram plots for both classes is determined. To quantify the voxels intensity values for both classes, a quantization scheme is selected.

Figure 3:
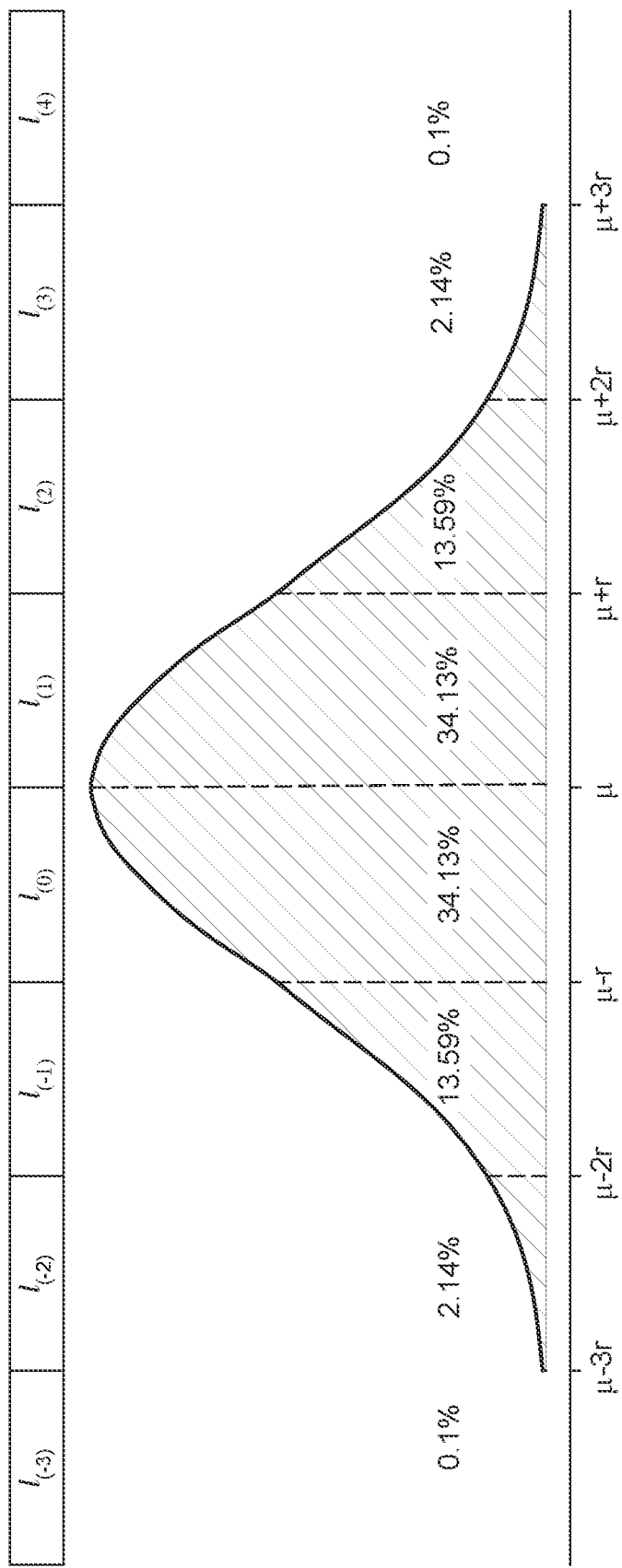
FIG. 3 illustrates a quantization scheme for the collected data.

A schematic diagram that illustrates the implementation strategy for this quantization scheme is shown in FIG. 3. The main parameters that can adjust the quantization scheme are the number of levels M and the resolution r. The scheme shown in FIG. 3 sets these values to M=8 and resolution r being one standard deviation $\sigma$. In this embodiment, the $k^{th}$ quantization interval, which is shown in FIG. 3 as being denoted as $l_k$ is defined as follows:

$$l_k=[\mu+(k-1)r,\mu+kr], \quad (2)$$

$$r=\alpha\sigma, \quad (3)$$

where $k=(-M)/2+1, \ldots, M/2$ and a is a positive scaling factor. Note that FIG. 3 shows 8 quantization intervals $l_k$, each having a length of r (i.e., all the intervals have the same length). FIG. 3 also indicates the number of elements of the sequence $X(n)$, in terms of percentages, that is present in each quantization interval $l_k$. While the example shown in FIG. 3 corresponds to M=8 quantization intervals, it is noted that other values may be selected for M, depending on the size and/or type of the input data. Parameters µ and σ in equations (2) and (3) are the average mean and standard deviation of the six subjects studied in FIG. 1, and they are defined as:

$$\mu = \frac{1}{6}\sum_{n=1}^{6} \mu_n \text{ and } \sigma = \frac{1}{6}\sum_{n=1}^{6} \sigma_n, \qquad (4)$$

where $\mu_n$ and $\sigma_n$ are the mean and the standard deviation of the voxels intensity for the $n^{th}$ subject. According to the probability theory and statistics, the probability that a Gaussian random variable h is greater than 3σ+µ is almost zero. This observation is a well-known rule in statistics and it is called the 3-sigma rule. Therefore, the most significant variabilities and randomness that characterizes a random sequence can still be observed if:

$$|h-\mu| \leq 3\sigma. \qquad (5)$$

Because the 3-sigma rule indicates that most of the information of a Gaussian random variable is located within 3σ+µ, the quantization interval length of the proposed quantization scheme is chosen to be an integer multiple of the standard deviation a as shown in FIG. 3.

The implementation strategy of the proposed quantization step 112 can be implemented in algorithm, as illustrated in FIG. 4. The input of this quantization scheme is the number of quantization levels M, the quantization resolution r, and a quantization centroid µ. The output of this quantization scheme is a symbol sequence Q(n) that can only take a finite set of symbols (i.e., $(q_1, \ldots, q_M)$, based on equation (400) in FIG. 4. When this scheme is applied to the real-valued voxel intensity samples for both classes (images and sentences), two matrices of size 40×16N, namely a picture matrix P and a sentence matrix S are generated. These two integer-valued matrices P and S will be utilized to generate the final VW-based feature vector.

The proposed quantization scheme illustrated in FIG. 4 can be applied to various types of datasets that are represented by the voxels intensity when a subject is performing a specific cognitive task (not necessarily viewing a picture or a sentence). The quantization parameters M and r are chosen based on the distribution of the real-valued voxels sequences that are related to such cognitive task.

The VW-based feature generation step 114 is now discussed. To extract the VW-based features, the PWM technique discussed above with regard to equation (1) and the quantization scheme illustrated in FIG. 4 are used. The VW-based features method would generate a reduced feature vector having only two values. These two values provide a probabilistic representation of the voxel pattern in response to two distinct cognitive tasks. This means, that the first value would indicate when an fMRI signal is associated with a picture and the second value would indicate when the fMRI signal is associated with a sentence. Those skilled in the art would understand that the picture and sentence type of data that needs to be classified are just one possible example and the same method may be used for any type of data. Having such a low-dimensionality feature vector (i.e., two-dimensional feature vector) can overcome the high-dimensionality of the feature vector associated with the traditional cognitive state predictions methods.

To generate such a low-dimensionality feature vector, the following two steps are being implemented. When the algorithm shown in FIG. 4 is applied to all the picture and sentence voxel intensity sequences (samples), two matrices (picture P and sentence S matrices) are constructed. Every entry of these matrices can take one of the M symbols $(q_1, \ldots, q_M)$ generated by the quantization algorithm. After that, two weighting matrices, namely the Picture Voxel Weight Matrix (PVWM) and the Sentence Voxel Weight Matrix (SVWM) are constructed the same way as the PWMs are generated in equation (1), i.e., a probability is calculated for the symbols $(q_1, \ldots, q_M)$ of the PVWM and SVWM matrices. For instance, when the number of quantization levels M of the algorithm of FIG. 4 is set to 6 and the resolution is r, the size of the two VW-based matrices PVWM and SVWM will be 6×16N. The matrix structure of the PVWM and the SVWM can take the following form:

$$\begin{pmatrix} 0.1 & 0.5 & 0.4 & 0.1 & \ldots & W(1, 16N) \\ 0.2 & 0.1 & 0.2 & 0.1 & \ldots & W(2, 16N) \\ 0.1 & 0.1 & 0.1 & 0.1 & \ldots & W(3, 16N) \\ 0.1 & 0.1 & 0.1 & 0.3 & \ldots & W(4, 16N) \\ 0.3 & 0.1 & 0.1 & 0.2 & \ldots & W(5, 16N) \\ 0.2 & 0.1 & 0.2 & 0.2 & \ldots & W(6, 16N) \end{pmatrix} \qquad (6)$$

where the weight W(i,j) indicates the probability that a certain voxel intensity will be quantized in one of the six quantization levels along the 40 picture trials or the 40 sentence trials (note that the matrix has q1 to q6 lines and 16N columns).

In this step, the frequencies of any of the M quantized levels along the picture and sentence sequences were used to derive the PVWM and the SVWM matrices. Next, these two matrices PVWM and SVWM are used to compute two scores for every symbol (integer-valued in this embodiment) sequence Q(n). These two scores indicate the likelihood of the sequence to be a picture or a sentence sequence. The two scores are computed for each sequence in the dataset and are calculated as follows: Let $S_j$ be the $j^{th}$ row of the sentence matrix S, and similarly $P_j$ be the $j^{th}$ row vector of P. From the previous step, $PVWM_{i,j}$ and $SVWM_{i,j}$ represent the probability of occurrence of the symbol $q_i$, where i=1, ..., M at a time instance j along the picture and the sentence sequences, respectively. Therefore, the two scores can be calculated for a level i of any integer-valued sequence Q(n) as follows:

$$\text{Score}_1(i) = \sum_{j=1}^{16N} PVWM_{Q(i),j}, \text{ and} \qquad (7)$$

$$\text{Score}_2(i) = \sum_{j=1}^{16N} SVWM_{Q(i),j}, \qquad (8)$$

Originally, every picture or sentence sample is represented by a 16N×1 feature vector. However, after applying the proposed feature generation methodology discussed above, this high-dimensional feature vector is mapped into a two-dimensional feature vector. The size of the full feature matrix is 80×2 where half of the samples represents the picture trials and the other half represents the sentence trials. A prediction model can be derived using this reduced feature vector, i.e., by calculating the scores described in equations (7) and (8), it is possible to predict whether a given fMRI signal reading corresponds to a subject seeing a picture or a sentence.

This means that the proposed VW-based feature generation methodology can be generalized to multi-classification problems. These classification problems may arise when one needs to distinguish between three or more cognitive tasks based on the fMRI dataset associated with these cognitive tasks. The number of VW-based matrices will be equal to the number of classes. The star/plus dataset used here provides only fMRI datasets for two cognitive tasks. Therefore, only two voxel weight matrices, namely PVWM and SVWM, were generated in this embodiment, as now discussed with regard to FIG. 5.

Figure 5:
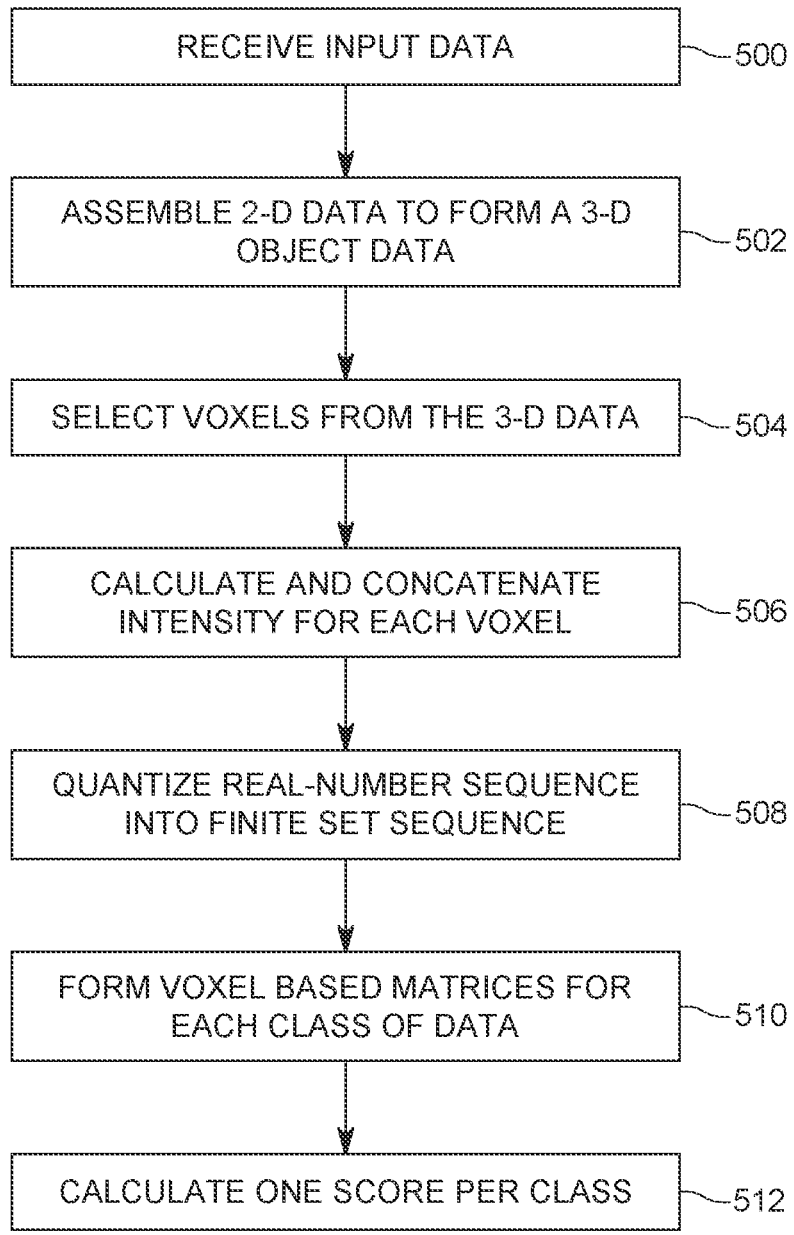
FIG. 5 is a flowchart of a method for automatically classifying input data into various classes.

FIG. 5 is a flowchart of a method for classifying information using a feature generation methodology that reduces a size of the feature vector. In step 500, the method receives input data. In the embodiments discussed above, the input data includes fMRI data. However, as previously discussed, other type of data may be received as the input data as long as the input data describes a three-dimensional object. In step 502, slices of the three-dimensional object are assembled together to form a three-dimensional representation of the object, as illustrated in FIG. 1, and voxels 106 of the data are selected in step 504. For the specific example discussed in this application, the size of the voxel 106 is selected based on a region of the brain that is believed to be most responsive to visualizing an image or a sentence. In step 506, the fMRI intensity for each voxel is calculated and then concatenated to produce a sequence X(n) for each sample, where n indicates the number of voxels. A sample corresponds to recoded intensities of the fMRI signal for a given subject, when exposed to the image or sentence, for a given amount of time. Note that the sequence X(n) includes real numbers, which are proportional in this embodiment to the fMRI signal intensity generated by the brain. However, if the input data includes another type of data, the sequence X(n) would include real numbers that describe that type of data. In step 508, the real-number sequence X(n) is quantized into a finite set sequence Q(n), based on the algorithm illustrated in FIG. 4. Thus, the finite set sequence Q(n) includes a finite number of symbols, where the symbols may be letters, numbers, or a mixture of them. Note that while the real-number sequence X(n) may have an infinite number of elements, the finite set sequence Q(n) must have a finite number of elements. The symbols of the finite set sequence Q(n) fall into corresponding intervals $l_k$, with k varying between 1 and M and M being the number of levels, and each level or interval being characterized by a resolution r. Note that each level or interval k has a corresponding symbol $q_k$, i.e., all the real-numbers from the sequence X(n) that would fall into the interval k, would be mapped to a same symbol $q_k$, as schematically illustrated in FIG. 1 by step 112. This mapping may be implemented using a Gaussian distribution as discussed above with regard to FIG. 2.

In step 510, the PVWM and SVWM matrices are formed based on the symbols $q_k$ of the finite set sequence Q(n). As previously discussed, each entry of the PVWM and SVWM matrices can take one of the M symbols $q_1$ to $q_M$, generated by the quantization step 508. The element of each of the PVWM and SVWM matrices indicates a probability that a certain voxel intensity (measured with the MRI device) will be quantized in one of the M quantization levels along the input data. For example, with regard to equation (6), the first line and first column element (0.1) indicates that the first sample would have a probability 0.1 to have the value q1, the second line, first column element (0.2) indicates that the first sample would have a probability 0.2 to have the value q2, and so on.

In step 512, two scores (described by equations (7) and (8)) are calculated based on the matrices PVWM and SVWM from step 508, for each level i for any value of the sequence Q(n). These scores indicate the likelihood of a sequence corresponding to a given sample to be a picture or sentence sequence. Note that every picture or sentence sample is originally represented (i.e., in the input data) by a 16N×1 feature vector. However, according to step 512, this high-dimensional feature vector 16N×1 is mapped into a two-dimensional feature vector, where the two components of this two-dimensional feature vector are given by the scores (8) and (9). Of course, if the input data includes more than 2 classes, a feature vector of larger size would be obtained.

The scores and the matrices PVWM and SVWM were tested against the star/plus dataset as now discussed. Due to the high-dimensionality of the original feature vector (16N×1) compared with the small number of samples (80 for the embodiment discussed above), the Leave-One-Out (LOO) cross-validation scheme was used to avoid a biased measure of test accuracy. The generated features were trained using a Logistic Regression (LR) classifier due to its simplicity and the satisfying results obtained with this model. Unlike most of the features used for classification, the VW-based features cannot be generated independently. This is because the VW-based features are correlated in the sense that the features cannot be extracted without the knowledge of the other training dataset (i.e., the whole training dataset needs to be processed together in order to generate the PVWM and SVWM matrices).

The PVWM and SVWM matrices are reconstructed for every training dataset (79 samples) that correspond to every fold of the 80 leave-one-out cross validation folds. The reason of doing this is that in any classification problem, the testing set should not be included in the learning stage. Hence, the PVWM and the SVWM matrices have to be re-calculated for every leave-one-out fold.

For every subject of the star/plus dataset, the voxel intensity sequence X(n) was first quantized using 6 levels and a resolution of one standard deviation (i.e., M=6 and r=σ), and then the VW-based features were generated as discussed above. To illustrate the effectiveness of the proposed VW-based features, the performance of the LR classifier trained on the proposed VW-based feature were compared with the best performing classifiers reported in literature. For a fair comparison, the performance of the proposed VW-based method was compared with prediction models that utilize feature vectors derived from 7 ROIs (CALC, LDLPFC, LIPL, LIPS, LOPER, LT and LTRIA), 4 ROIs (CALC, LIPL, LIPS and LOPER) and the "CALC" ROI. In the literature, the authors applied the Naive Bayesian (NB) and the Support Vector Machine (SVM) classifiers to feature vectors that were derived from all the 7 ROI, respectively. Table I in FIG. 6 reports the results obtained by using the feature vectors derived from the "CALC" ROI under Method 1 (described in [3]), Method 2 (described in [8]) and the proposed VW-based method. In addition, Tables II and III, shown in FIGS. 7 and 8, respectively, depict the results of the classifiers when they utilize feature vectors derived from the 4 ROIs and the 7 ROIs, respectively.

The two metrics used to compare these classifiers are the size (i.e., dimension) of the feature vector and the prediction accuracy. To illustrate the overall performance of each method, the average feature size and the average accuracy were computed. From Table I, the average accuracy of the cognitive state prediction problem obtained by the VW-based prediction method was improved by about 2.3% and 14% compared to that obtained by Method 2 and Method 1, respectively. These prediction performances were achieved when only the 'CALC' ROI was used for feature generation. Tables II and III show that the VW-based method improves the average accuracy of Method 1 by 4.2% and 4.7% when 4 ROIs and 7 ROIs were used for feature generation, respectively. Similarly, the VW-based method outperformed the average accuracy of Method 2 by 1.43% and 2% when 4 ROIs and 7 ROIs were used for feature generation, respectively. In all the cases, the VW-based method reduced significantly (two-dimensional) the size of the feature vector used when all the 7 ROIs were used for feature generation. In this regard, note that Method 1 had a feature vector with the size in the thousands and Method 2 had a feature vector with the size in the hundreds.

Table IV in FIG. 9 illustrates the sensitivity analysis that was performed, in which the average accuracy across the six subjects was computed for every scenario. The purpose of this analysis was to investigate the impact of the relationship between the statistical measures ($\mu$ and $\sigma$) of the voxel intensity sequence X(n) and the quantization parameters (M and r) on the average accuracy of the prediction model. From Table IV, one can achieve a consistent (i.e., stable) prediction model with 100% average accuracy when the number of quantization level M is greater than or equal to 6, and the resolution r is between 0.8 $\sigma$ and 1.2 $\sigma$.

Generally, when the resolution r is smaller than or equal to 0.6 $\sigma$, the average accuracy for every subject fluctuates and goes down for most of the scenarios. One possible reason for this phenomenon is the overfitting issue that may happen when the resolution gets very small and the number of levels increases. On the other hand, when the resolution r increases (i.e., r>=1.4$\sigma$, which means $\alpha$>=1.4), the two VW-based matrices PVWM and SVWM become sparse. As a result, the generated features, under this choice of quantization parameters for both classes, will not be significantly different from each other. Consequently, the average accuracy of the LR classifier decreases as the resolution increases, regardless of the number of intervals M as shown in Table IV.

Figure 10:
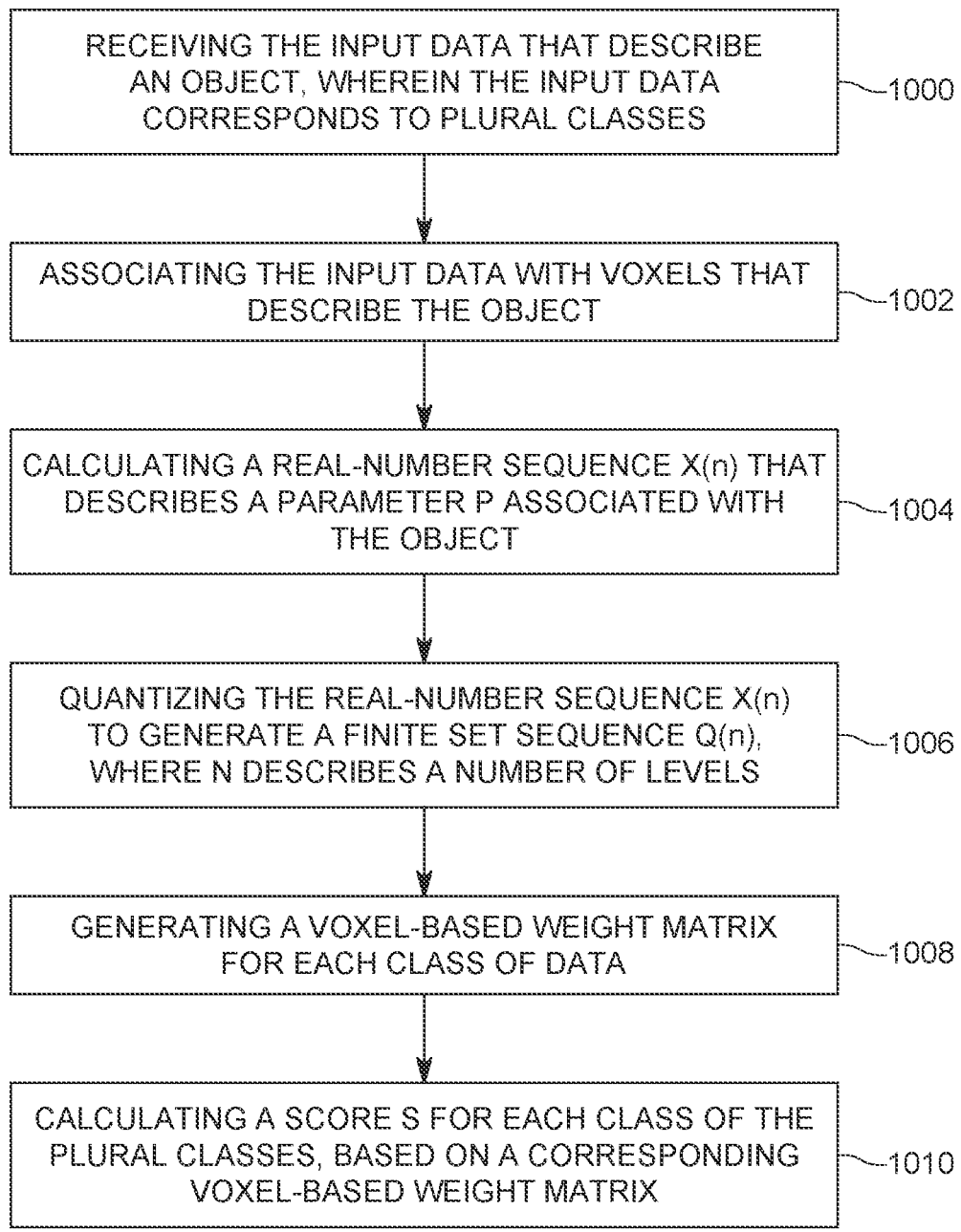
FIG. 10 is a flowchart of a method for calculating a score for various sequences of the data according to each class.

A method for classifying input data is now discussed with regard to FIG. 10. The method includes a step 1000 of receiving the input data 104 that describe an object 101, where the input data 104 corresponds to plural classes, a step 1002 of associating the input data 104 with voxels 106 that describe the object 101, a step 1004 of calculating a real-number sequence X(n) that describes a parameter P associated with the object 101, a step 1006 of quantizing the real-number sequence X(n) to generate a finite set sequence Q(n), where n describes a number of levels, a step 1008 of generating a voxel-based weight matrix for each class of data, and a step 1010 of calculating a score S for each class of the plural classes, based on a corresponding voxel-based weight matrix. The score S is a number that indicates a likelihood that the input data associated with a given voxel at a given time belongs to a class of the plural classes.

The object may be the brain of a patient and the input data may correspond to magnetic resonance images (MRI) of the brain. In one application, the plural classes includes first and second classes. In another application, the first class corresponds to MRI signals generated as the brain is being exposed to a picture and the second class corresponds to MRI signals generated as the brain is being exposed to a sentence and each voxels is associated with a part of the brain. In one application, the parameter is an intensity of the MRI signal.

The step of quantizing may include mapping each element of the real-number sequence X(n) to one of M symbols. In one application, M describes to total number of levels. The elements of the real-number sequence X(n) correspond to measured intensities of signals associated with magnetic resonance images (MRI). In one application, M is larger than or equal to 6.

The method may also include a step of generating a voxel-based weight image matrix and a voxel-based weight sentence matrix, and/or a step of adding together all the column elements j of a corresponding voxel-based weight matrix, for a given line i, for all the voxels, to obtain the score S.

Figure 11:
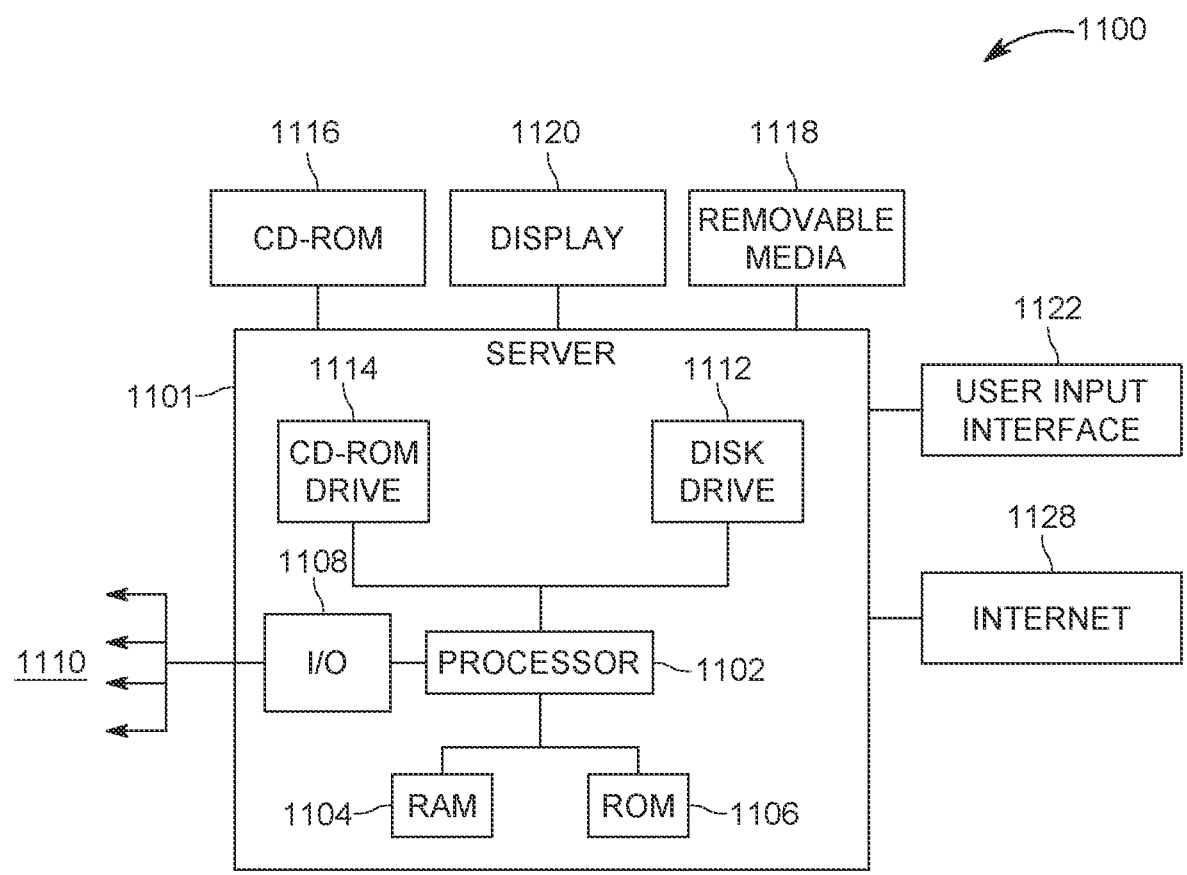
FIG. 11 is a computing device in which the above methods may be implemented.

The above-discussed procedures and methods may be implemented in a computing device as illustrated in FIG. 11. Hardware, firmware, software or a combination thereof may be used to perform the various steps and operations described herein. Computing device 1100 suitable for performing the activities described in the exemplary embodiments may include a server 1101. Such a server 1101 may include a central processor (CPU) 1102 coupled to a random access memory (RAM) 1104 and to a read-only memory (ROM) 1106. ROM 1106 may also be other types of storage media to store programs, such as programmable ROM (PROM), erasable PROM (EPROM), etc. Processor 1102 may communicate with other internal and external components through input/output (I/O) circuitry 1108 and bussing 1110 to provide control signals and the like. Processor 1102 carries out a variety of functions as are known in the art, as dictated by software and/or firmware instructions.

Server 1101 may also include one or more data storage devices, including hard drives 1112, CD-ROM drives 1114 and other hardware capable of reading and/or storing information, such as DVD, etc. In one embodiment, software for carrying out the above-discussed steps may be stored and distributed on a CD-ROM or DVD 1116, a USB storage device 1118 or other form of media capable of portably storing information. These storage media may be inserted into, and read by, devices such as CD-ROM drive 1114, disk drive 1112, etc. Server 1101 may be coupled to a display 1120, which may be any type of known display or presentation screen, such as LCD, plasma display, cathode ray tube (CRT), etc. A user input interface 1122 is provided, including one or more user interface mechanisms such as a mouse, keyboard, microphone, touchpad, touch screen, voice-recognition system, etc.

Server 1101 may be coupled to other devices, such as imaging device (e.g., MRI device), detectors, etc. The server may be part of a larger network configuration as in a global area network (GAN) such as the Internet 1128, which allows ultimate connection to various landline and/or mobile computing devices.

The disclosed embodiments provide a novel method and system for classifying input data according to classes based on a quantification scheme and usage of voxel-weight matrices. It should be understood that this description is not intended to limit the invention. On the contrary, the exemplary embodiments are intended to cover alternatives, modifications and equivalents, which are included in the spirit and scope of the invention as defined by the appended claims. Further, in the detailed description of the exemplary embodiments, numerous specific details are set forth in order to provide a comprehensive understanding of the claimed invention. However, one skilled in the art would understand that various embodiments may be practiced without such specific details.

Although the features and elements of the present exemplary embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

REFERENCES

[1] Tom M Mitchell, Rebecca Hutchinson, Radu S Niculescu, Francisco Pereira, Xuerui Wang, Marcel Just, and Sharlene Newman, "Learning to decode cognitive states from brain images," Machine Learning, pp. 145-175, 2004.
[2] Carlos Cabral, Margarida Silveira, and Patricia Figueiredo, "Decoding visual brain states from fmri using an ensemble of classifiers," Pattern Recognition, pp. 2064-2074, 2012.
[3] Xuerui Wang and Tom Mitchell, "Detecting cognitive states using machine learning," 2002.
[4] Hariharan Ramasangu and Neelam Sinha, "Cognitive state classification using transformed fmri data," in Signal Processing and Communications (SPCOM), 2014, pp. 1-5.
[5] Fahad Albalawi, Abderrazak Chahid, Xingang Guo, Somayah Albaradei, Arturo Magana-Mora, Boris R. Jankovic, Mahmut Uludag, Christophe Van Neste, Magbubah Essack, Taous-Meriem Laleg-Kirati, and Vladimir B. Bajic, "Hybrid model for efficient prediction of poly(a) signals in human genomic dna," Methods, Provisionally Accepted.
[6] Robert M. Gray and David L. Neuhoff, "Quantization," IEEE Transactions on Information Theory, pp. 2325-2383, 1998.
[7] S. Sinha, "On counting position weight matrix matches in a sequence, with application to discriminative motif finding," Bioinformatics, vol. 22, pp. e454-e463, 2006.
[8] J Siva Ramakrishna and Hariharan Ramasangu, "Classification of cognitive state using statistics of split time series," in India Conference (INDICON), 2016 IEEE Annual, 2016, pp. 1-5.

What is claimed is:

1. A method for classifying input data of a 3-dimensional object, the method comprising:
   receiving the input data that describe the object, wherein the input data corresponds to plural classes;
   associating the input data with voxels that describe the object;
   calculating a real-number sequence X(n), which is associated with a measured parameter P that describes the object;
   quantizing the real-number sequence X(n) to generate a finite set sequence Q(n), where M describes a number of levels;
   generating a voxel-based weight matrix for each class of the input data; and
   calculating a score S for each class of the plural classes, based on a corresponding voxel-based weight matrix, wherein the score S is a number that indicates a likelihood that the input data associated with a given sample belongs to a class of the plural classes.

2. The method of claim 1, wherein the object is a brain and the input data corresponds to magnetic resonance images (MRI) of the brain.

3. The method of claim 2, wherein the plural classes includes first and second classes.

4. The method of claim 3, wherein the first class corresponds to MRI signals generated as the brain is being exposed to a picture and the second class corresponds to MRI signals generated as the brain is being exposed to a sentence.

5. The method of claim 4, wherein each voxels is associated with a volume of the brain.

6. The method of claim 2, wherein the parameter is an intensity of the MRI signal.

7. The method of claim 1, wherein the step of quantizing comprises:
   mapping each element of the real-number sequence X(n) to one of n symbols.

8. The method of claim 7, wherein M describes to total number of levels.

9. The method of claim 7, wherein elements of the real-number sequence X(n) correspond to measured intensities of signals associated with magnetic resonance images (MRI).

10. The method of claim 7, wherein M is larger than or equal to 6.

11. The method of claim 7, wherein the step of generating a voxel-based weight matrix comprises:
   generating a voxel-based weight image matrix and a voxel-based weight sentence matrix.

12. The method of claim 1, wherein the step of calculating a score S comprises:
   adding together all the column elements j of a corresponding voxel-based weight matrix, for a given line i, for all the voxels.

13. A computing device for classifying input data of a 3-dimensional object, the computing device comprising:
   an interface for receiving the input data that describe the object, wherein the input data corresponds to plural classes; and
   a processor connected to the interface and configured to,
   associate the input data with voxels that describe the object;
   calculate a real-number sequence X(n) that describes a parameter P associated with the object;
   quantize the real-number sequence X(n) to generate a finite set sequence Q(n), where M describes a number of levels;
   generate a voxel-based weight matrix for each class of data; and
   calculate a score S for each class of the plural classes, based on a corresponding voxel-based weight matrix, wherein the score S is a number that indicates a likelihood that the input data associated with a given sample belongs to a class of the plural classes.

14. The computing device of claim 13, wherein the object is a brain and the input data corresponds to magnetic resonance images (MRI) of the brain.

15. The computing device of claim 14, wherein the plural classes includes first and second classes.

16. The computing device of claim 15, wherein the first class corresponds to MRI signals generated as the brain is being exposed to a picture and the second class corresponds to MRI signals generated as the brain is being exposed to a sentence.

17. The computing device of claim 16, wherein each voxel is associated with a part of the brain and the parameter is an intensity of the MRI signal.

18. The computing device of claim 13, wherein the processor is further configured to:
   map each element of the real-number sequence X(n) to one of n symbols,
   wherein M describes to total number of levels.

19. The computing device of claim 18, wherein the processor is further configured to:
   generate a voxel-based weight image matrix and a voxel-based weight sentence matrix.

20. The computing device of claim 13, wherein the processor is further configured to:
   add together all the column elements j of a corresponding voxel-based weight matrix, for a given line i, for all the voxels.

* * * * *